United States Patent [19]

Bennett

[11] Patent Number: Plant 5,259

[45] Date of Patent: Jul. 17, 1984

[54] MINIATURE ROSE PLANT

[76] Inventor: Cecilia L. D. Bennett, 489 Minot Ave., Chula Vista, Calif. 92010

[21] Appl. No.: 463,534

[22] Filed: Feb. 3, 1983

[51] Int. Cl.[3] ..... A01H 5/00

[52] U.S. Cl. ..... Plt./10

[58] Field of Search ..... Plt./10

*Primary Examiner*—Robert E. Bagwill

[57] ABSTRACT

The subject of the present disclosure is a new and distinct variety of miniature rose plant characterized by its brilliant orange-red bloom and hybrid tea form.

1 Drawing Figure

1

The present invention relates to a new and distinct variety of a hardy, dwarf, miniature bush plant of the miniature class; the variety being primarily characterized as an orange-red.

The variety is further characterized by:

Long-stemmed show quality blooms, usually blooming one to a stem.

A slight tea fragrance.

Buds and flowers comparable in color to "Tropicana" a hybrid tea rose plant introduced by Jackson and Perkins in 1962. (U.S. Plant Pat. No. 2,701).

The plant ranges in height from 12 to 20 inches. The branches are long, slender but sturdy and hold the bloom very erect. Grows equally well in hothouse or outdoors.

The present variety of miniature rose was originated by me at Tiny Petal's Nursery, located at Chula Vista, Calif., under careful observation, and is a cross of "Orange Honey" a miniature (U.S. Plant Pat. No. 4,496) as the pollen parent, and "Futura" a hybrid tea, (U.S. Plant Pat. No. 3,569) an orange-red, introduced by Jackson and Perkins in 1975, as the seed parent.

Subsequent to origination of the variety I successfully reproduced it at Tiny Petal's Nursery located at aforesaid with reproductions coming true in all respects.

The color photographs illustrate the variety.

Referring now specifically to the new and distinct variety of miniature rose plant, the following is a detailed description thereof in outline; all major color plate identification being by reference to the British Colour Council Horticultural Chart.

Type: Hardy; dwarf; compact; seedling; greenhouse; outdoors; cut flowers; garden decoration; potted plant.

Class: Miniature.

Variety name: "Hotshot".

Flowers borne: One to a stem.

Quantity of bloom: Abundant both in hothouse or outdoors.

Bud:

*Peduncle.*—Long; slender; erect; reddish; 1¾ to 2 inches in length.

*Hairs.*—Very minute; reddish.

*Before calyx breaks.*—Size small. Form—ovoid; sepals extending well over the end of the bud. Color—medium green with reddish tinge.

*As calyx breaks.*—Color reddish with a tinge of creamy yellow. Opens well in all weather.

Bloom:

2

*Size when fully open.*—Averaging from 1½ to 1¾ inches in diameter.

*Petalage.*—Double averaging from 20 to 25 petals, arranged regularly.

*Form.*—Center petals slightly smaller than outer petals. Opens slowly with gentle reflexing of the petals. Open flower reveals a showy display of stamens.

Petals: Good substance; matt surface topside and under side of petals.

*Shape.*—Outside petals, broad lanceolate with minute tip; intermediate petals, broad lanceolate with minute tip, inside petals, broad lanceolate without tip.

Color: Newly opened flower as grown at Chula Vista, Calif.

*Outer petals.*—Topside surface scarlet 19, page 19, with a small tip of mimosa yellow 602, page 143, at the base of the petal.

*Outer petal.*—Underside surface scarlet 19, page 19, with a small tip of mimosa yellow 602, page 143, at the base of the petal.

*Intermediate petal.*—Topside surface scarlet 19, page 19, with a small tip of mimosa yellow at the base of the petal.

*Intermediate petal.*—Underside surface scarlet 19 page 19, with small tip of mimosa yellow 602, page 143, at the base of the petal.

*Center petal.*—Topside surface scarlet 19, page 19, with small tip of mimosa yellow at the base of the petal.

*Center petal.*—Underside petal scarlet 19, page 19, with a small tip of mimosa yellow 602, page 143, at the base of the petal.

Behavior: Opens well in all weather. Opens slowly. Form—exhibition: color scarlet. The bloom has excellent lasting qualities—holds color with very little fading.

Reproductive organs:

*Stamens.*—Abundant, arranged evenly around pistil.

*Filament.*—Varying lengths.

*Pollen.*—Abundant.

*Pistil.*—Short and abundant.

*Styles.*—Short, irregular.

*Ovaries.*—All encased in calyx.

*Hips.*—None.

*Sepals.*—Long spear shaped.

Foliage:

*Leaves.*—Compound of five and seven, small.

*Leaflets.*—Shape—broad; arrow shaped.

*Margin.*—Very serrated.

*Color.*—Medium green, matt surface.

Rachis: Medium length; underside smooth.

*Stipule.*—Medium length; medium width.

Growth:

*Habit.*—Dwarf, bushy, much branched.

*Growth.*—Vigorous.

*Canes.*—Long, straight, slender, strong.

*Main stem.*—Color, medium green.

*Thorns.*—Small, slender, reddish.

*Prickles.*—A few.

*Branches.*—Color, medium green.

*Thorns.*—Reddish, quite a few.

The plant is easy to grow from cuttings or buds.

The miniature rose plant and its flowers as herein described may vary in slight detail due to climatic, soil and cultural conditions under which the variety may be grown; the present description being of the variety as grown by me at Chula Vista, Calif.

I claim:

1. A new and distinct variety of miniature rose plant of hardy, dwarf, bushy, much branched habit, substantially as illustrated and described, characterized by buds and flowers of orange-red.

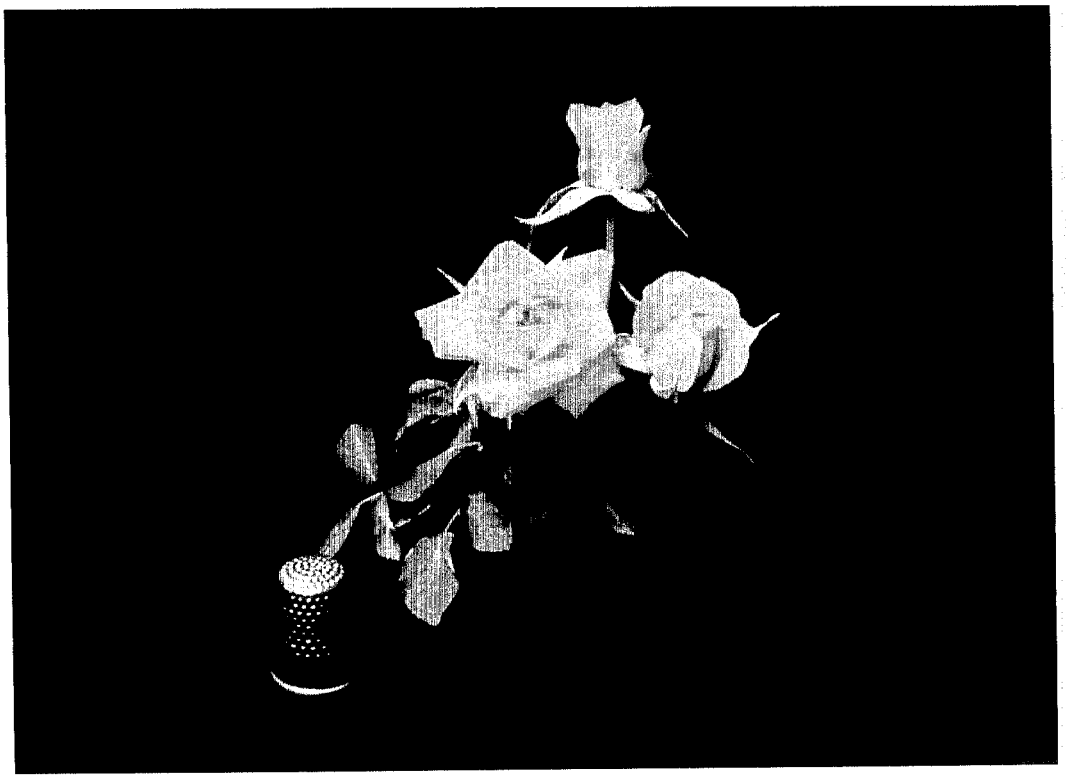

* * * * *